(12) United States Patent
Martin et al.

(10) Patent No.: US 6,726,940 B2
(45) Date of Patent: Apr. 27, 2004

(54) USE OF AT LEAST ONE EXTRACT OF THE GENUS CHRYSANTHEMUM FOR ASSISTING SKIN AND/OR HAIR PIGMENTATION

(75) Inventors: Richard Martin, Rochecorbon (FR); Béatrice Belcour-Castro, La Riche (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/987,204

(22) Filed: Nov. 13, 2001

(65) Prior Publication Data

US 2002/0122812 A1 Sep. 5, 2002

Related U.S. Application Data

(63) Continuation of application No. 09/508,991, filed as application No. PCT/FR98/01958 on Sep. 14, 1998.

(30) Foreign Application Priority Data

Sep. 18, 1997 (FR) .............................. 97 11648

(51) Int. Cl.$^7$ .............................. A61K 7/26; A61K 7/00; A61K 7/06
(52) U.S. Cl. ........................ 424/764; 424/725; 424/774; 424/410; 514/880
(58) Field of Search .............................. 424/401, 195.1; 514/880

(56) References Cited

U.S. PATENT DOCUMENTS 4,911,925 A 3/1990 Shatkina et al.

FOREIGN PATENT DOCUMENTS

CN 93110975.2 * 11/1994
JP 61033123 A * 2/1986

OTHER PUBLICATIONS

Shibahashi, R. et al. JP 361033123 A (Feb. 1986), Abstract of JP 61033123 A.*
Wang, N., English translation of CN 93110975.2, (Nov. 1994).*

Knox, R., "How & Why", (Jun. 15, 1992), Boston Globe, starting p. 30 (electronic copy pp. 1–2).*

Database WPI, Week 9726 Derwent Publications Ltd., London, GB; AN 97–281465 XP002062463 & CN 1 102 340 A (Liu), May 10, 1994, see abstract.

Database WPI, Week 9543, Derwent Publication Ltd., London, GB; AN 95–328816 XP002062464 & CN 1 094 278 A (Wang), cited in the application, see abstract.

Database WPI, Week 8714, Derwent Publications Ltd., London, GB; AN 87–099079 XP002062465 & JP 62–048611 A (Shiseido Co), cited in the application, see abstract.

Patent Abstracts of Japan, vol. 7, No. 248 (C–193) & JP 58 135803 A (Noriko Sugano), see abstract.

Japanese Patent Abstracts, JP 07025746 A, Akamatsu et al., (1995), Abstract.

Derwent World Patent Index, AN 1995–308991, Kao Corp., (1995), JP 0706657 A, Abstract, London, GB.

Wang, Translation of (CN1094278, (1994), Pure Natural Medicine Type Physiotherapy Health Hair Care Shape Foam Agent). U.S. PTO, (2001).

Azuma et al., Translation of (JP07206657A, (1995) Whitening Agent and Skin External Preparation Containing the Same), U.S. PTO, (2000).

Reid, D., A Handbook of Chinese Healing Herbs, (1995), Barnes & Noble, Inc., p. 83–4.

* cited by examiner

*Primary Examiner*—Sreeni Padmanabhan
*Assistant Examiner*—Gina C. Yu
(74) *Attorney, Agent, or Firm*—Burns, Doane, Swecker & Mathis L.L.P.

(57) ABSTRACT

The invention concerns the use in a cosmetic composition or for preparing a pharmaceutical composition of at least a plant extract of the genus Chrysanthemum for stimulating skin and/or hair pigmentation. The invention also concerns a composition containing at least one active principle and an extract of at least a plant of the genus Chrysanthemum.

16 Claims, No Drawings

USE OF AT LEAST ONE EXTRACT OF THE GENUS CHRYSANTHEMUM FOR ASSISTING SKIN AND/OR HAIR PIGMENTATION

This application is a continuation of patent application Ser. No. 09/508,991 filed Jul. 11, 2000 which is a 371 of PCT/FR98/01958 filed Sep. 14, 1998.

The invention relates to the use of at least one extract of at least one plant of the genus Chrysanthemum in a composition for assisting skin and/or hair pigmentation.

The color of the human hair and skin is a function of different factors and especially of the seasons of the year, the race, the sex and the age. It is principally determined by the concentration in the keratinocytes of the melanin produced by the melanocytes. The melanocytes are the specialized cells which synthesize melanin through particular organelles, the melanosomes.

The synthesis of melanin or melanogenesis is particularly complex and schematically involves the following principal steps:

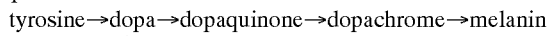

tyrosine→dopa→dopaquinone→dopachrome→melanin

Tyrosinase (monophenol dihydroxyl phenylalanine: oxygen oxidoreductase/EC 1,14,18,1) is the essential enzyme intervening in this sequence of reactions. It especially catalyses the conversion reaction of tyrosine into dopa (dihydroxyphenylalanine) and the conversion reaction of dopa into dopaquinone.

In the epidermis, the melanocyte is involved in the epidermal melanin unit which contains a melanocyte surrounded by approximately 36 neighbouring keratinocytes. All individuals, without distinction of phototype, have approximately the same number of melanocytes for a given cutaneous zone. The ethnic differences, in terms of pigmentation, are not due to the number of melanocytes, but to the properties of their melanosomes. The melanosomes are aggregated into complexes and are of small size. These are highly specialized organelles whose unique function is the production of melanin. They originate from the endoplasmic reticulum in the form of spherical vacuoles called premelanosomes. The premelanosomes contain an amorphous protein substrate, but no melanogenic enzymes. In the course of maturation of the premelanosome, the amorphous substrate organizes into a fibrillar structure orientated in the longitudinal axis of the melanosome. Four stages of development of the melanosome are distinguished corresponding to the intensity of melanization. Melanin is deposited uniformly on the internal fibrillar network of the melanosome and the opacity of the organelle increases up to saturation. As the melanin is synthesized in the melanosomes, these move from the perinuclear region towards the end of the dendrites of the melanocytes. By phagocytosis, the end of the dendrites is captured by the keratinocytes, the membranes are degraded and the melanosomes are redistributed in the keratinocytes.

Although the level of melanin varies from one population to another, the quantity of tyrosinase does not vary significantly and the level of messenger RNAs of the tyrosinase is identical in white or black skins. The variations in melanogenesis are therefore due to variations either in the activity of the tyrosinase or in the capacity of the keratinocytes to phagocytose the melanosomes.

It is known that in the majority of populations the brown color of the skin and the preservation of a constant coloration of the hair are important aspirations.

In addition, pigmentation diseases exist such as, for example, vitiligo, which is an auto-immune disease which is characterized by the appearance of white patches on the skin linked to a pigmentation defect.

There is therefore a real need for a product facilitating and/or improving the pigmentation of the skin and/or the hair.

Numerous solutions have been proposed in the field of artificial coloration by supply of sensible exogenous colorants to give to the skin and/or the hair a coloration which is the closest possible to that which is naturally or, in the field of natural coloration, by stimulation of the natural routes of pigmentation.

For example, in the documents WO-A-9517161, WO-A-9511003, WO-A-9501773, WO-A-9404674, WO-A-9404122, EP-A-585018, WO-A-9310804, WO-A-9220322 or WO-A-9107945 solutions have been proposed which are as varied as compositions containing a phosphodiesterase inhibitor, the use of prostaglandins, DNA fragments or even tyrosine derivatives.

Excellent results are admittedly obtained by the solutions proposed in the prior art, but the compounds used often have non-negligible side effects or are complex mixtures which do not have any specificity.

The discovery of substances having an effect on pigmentation of the skin and/or the hair without having inconvenient side effects remains a major research objective.

The applicant has now discovered that at least one extract of at least one plant of the genus Chrysanthemum has an activatory effect on melanogenesis.

The plants of the genus Chrysanthemum are used in the prior art in compositions having depigmenting properties (JP07025745, JP07025746), compositions favouring the growth of the hair and/or combating hair loss (FR2659014, EP569667, DE4330597, DE4312109, JP8081336, JP84154598, JP02048514), anti-dandruff compositions (KR9006824, JP62153211) or compositions for maintaining the suppleness, the hydration and the sheen of the skin (JP62048611). The patent applications CN1094278 and CN1094279 relate to compositions for natural hair treatment. These compositions have a variety of properties (embellishment of the hair, fixing, promotion of the blood circulation and the growth of the hair, bactericidal, antipruritic, anti-dandruff) among which an anti-white-hair action is mentioned. These compositions are in fact a mixture of 2 components each formed of extracts of at least 9 plants, without it being possible to attribute one of the numerous properties cited to one more than another.

To the knowledge of the applicant, use as an active principle of a plant extract of the genus Chrysanthemum has never been claimed for assisting the pigmentation of the skin and/or the hair.

The invention therefore relates to the use in a cosmetic composition or for the preparation of a pharmaceutical composition, as active principle, of a sufficient quantity of at least one extract of at least one plant of the genus Chrysanthemum, this extract or the composition being intended to increase the pigmentation of the skin and/or of the hair.

The invention likewise relates to the use in a cosmetic composition or for the preparation of a pharmaceutical composition, as active principle, of a sufficient quantity of at least one extract of at least one plant of the genus Chrysanthemum for assisting melanogenesis.

The extract of at least one plant of the genus Chrysanthemum can be any extract prepared from any plant material originating from a plant of the genus Chrysanthemum.

The composition can contain at least one extract of at least one plant of the genus Chrysanthemum obtained from material originating from a plant cultivated in vivo or originating from in vitro culture.

In vivo cultivation is understood as meaning any cultivation of conventional type, that is to say in soil in the open air or in a greenhouse, or alternatively outside the soil.

It is thus possible to use, for example, according to the invention an extract of different parts of the plant, leaves, flowers, stems, roots, undifferentiated cells, alone or as a mixture, whether the plant is cultivated in vivo or in vitro.

The selection pressure imposed by the physicochemical conditions during the growth of the plant cells in vitro allows a plant material to be obtained which is standardized and available throughout the year unlike the plant cultivated in vivo.

In vitro culture is understood as meaning all of the techniques known to the person skilled in the art which artificially allow the obtainment of a plant or of a part of a plant.

Preferably, an extract obtained from plant material cultivated in vivo is used and even more preferentially an extract obtained from leaves of plants of the genus Chrysanthemum cultivated in vivo.

The genus Chrysanthemum belongs to the family of Compositae which itself belongs to the order of Asteracae (or Asterales).

The genus Chrysanthemum contains approximately 200 species native to Europe and Asia, amongst which it is possible to mention *Chrysanthemum hortorum, Chrysanthemum morifolium, Chrysanthemum coronarium, Chrysanthemum myconis, Chrysanthemum sagitum, Chrysanthemum indicum*, or alternatively *Chrysanthemum segetum*.

Preferentially, according to the invention a plant is used originating from the species *Chrysanthemum morifolium*.

The species *Chrysanthemum morifolium* comprises numerous varieties amongst which it is possible to mention the variety sinense, preferentially used according to the invention.

Extract of at least one plant of the genus Chrysanthemum is understood as meaning both a crude mixture of parts of the plant coarsely reduced to pieces and of the extraction solvent as well as preparations elaborated from the solubilized active principles during extraction. An extract which is particularly utilizable according to the invention is produced by the fine grinding of parts of the plant followed by maceration in the extraction solvent and finally filtration. Quite obviously, the extract according to the invention can be each of the extracts thus obtained used on its own or as a mixture with one or more of the other extracts.

Any method of extraction known to the person skilled in the art can be used according to the invention.

It is possible to mention, in particular, aqueous and alcoholic, especially ethanolic, extracts, and aqueous-alcoholic extracts.

Whatever the form of the extract which it is intended to use, the techniques used to obtain it are those generally described in the prior art and well known to the person skilled in the art.

It is likewise possible to use an extract prepared by the method described in the French Patent Application No. 95-02379.

Thus, in a first step the plant material is ground in a cold aqueous solution, in a second step the particles in suspension are eliminated from the aqueous solution originating from the first step, and in a third step the aqueous solution originating from the second step is sterilized. This aqueous solution corresponds to the extract. On the other hand, the first step can advantageously be replaced by a simple freezing operation of the plant tissues (for example at −20° C.), followed by an aqueous extraction taking over the second and third steps described above.

Whatever the mode of preparation used according to the invention, subsequent steps aiming at assisting preservation and/or stabilization can be added without for all that modifying the actual nature of the extract. Thus, for example, the extract obtained can be lyophilized by any conventional lyophilization method. A powder is thus obtained, which can be used directly or else mixed in an appropriate solvent before use.

An Aqueous Extract is Preferentially Used According to the Invention

Detailed methods of extract preparation which can be used according to the invention are additionally given in the examples.

The quantity of extract of at least one plant of the genus Chrysanthemum contained in the composition of the invention is, of course, a function of the effect sought and of the form of the extract used in the composition. It can therefore vary to a wide extent.

To give an order of size, whatever its nature, the composition can contain an extract of at least one plant of the genus Chrysanthemum in a quantity representing from 0.01% to 15% of the total weight of the composition and preferentially in a quantity representing from 1% to 5% of the total weight of the composition.

The compositions according to the invention are essentially intended to increase the pigmentation of the skin and/or of the hair and/or to stimulate melanogenesis. Whatever its nature, the composition of the invention is essentially applied to the skin (on any cutaneous area of the body) and/or the hair.

According to the method of administration, the composition according to the invention can be present in any of the pharmaceutical forms normally used.

For topical application to the skin, the composition can have the form especially of an aqueous or oily solution or of a dispersion of the lotion or serum type, of emulsions of liquid or semi-liquid consistency of the milk type, obtained by dispersion of a fatty phase in an aqueous phase (O/W) or conversely (W/O), or of suspensions or emulsions of soft consistency of the aqueous or anhydrous cream or gel type, or alternatively of microcapsules or microparticles, or of vesicular dispersions of ionic and/or non-ionic type. These compositions are prepared according to the usual methods.

They can likewise be used for the hair in the form of aqueous, alcoholic or aqueous-alcoholic solutions, or in the form of creams, gels, emulsions, foams or even in the form of aerosol compositions likewise comprising a propellant under pressure.

The quantities of the different constituents of the compositions according to the invention are those conventionally used in the fields considered.

These compositions especially form cleansing, protection, treatment or care creams for the face, for the hands, for the feet, for the major anatomical folds or for the body (for example day creams, night creams, make-up removal creams, foundation creams, suntan creams), liquid foundations, make-up removal milks, protection or care body milks, suntan milks, lotions, gels or foams for the care of the skin, such as cleansing lotions, suntan lotions, artificial tanning lotions, compositions for the bath, deodorant compositions comprising a bactericidal agent, gels or aftershave lotions, epilatory creams, compositions against insect stings, analgesic compositions, compositions for treating certain diseases of the skin such as eczema, rosacea, psoriasis, lichens and severe pruritus.

The compositions according to the invention can likewise consist of solid preparations forming cleansing soaps or cakes.

The compositions can also be packaged in the form of an aerosol composition likewise comprising a propellant under pressure.

The composition according to the invention can also be a composition for hair care, and especially a shampoo, hair setting lotion, a treatment lotion, a hair-styling cream or gel, a dye composition (especially oxidation dyes) possibly in the form of dyeing shampoos, restructuring lotions for the hair, a permanent waving composition (especially a composition for permanent waving for the first time), a hair-loss lotion or gel, an antiparasitic shampoo, etc.

When the composition is an emulsion, the proportion of the fatty phase can range from 5% to 80% by weight, and preferably from 5% to 50% by weight with respect to the total weight of the composition. The oils, the waxes, the emulsifiers and the co-emulsifiers used in the composition in emulsion form are selected from those conventionally used in the cosmetic field. The emulsifier and the co-emulsifier are present, in the composition, in a proportion ranging from 0.3% to 30% by weight, and preferably from 0.5 to 20% by weight with respect to the total weight of the composition. The emulsion can, in addition, contain lipid vesicles.

When the composition is a solution or an oily gel, the fatty phase can represent more than 90% of the total weight of the composition.

In a known manner, the cosmetic composition can likewise contain adjuvants customary in the cosmetic field, such as hydrophilic or lipophilic gelling agents, hydrophilic or lipophilic additives, preservatives, antioxidants, solvents, perfumes, bulking agents, filters, odour absorbers and coloring materials. The quantities of these different adjuvants are those conventionally used in the cosmetic field, and, for example, from 0.01% to 10% of the total weight of the composition. These adjuvants, according to their nature, can be introduced into the fatty phase, into the aqueous phase and/or into lipid spherules. Oils or waxes which can be used in the invention and which can be mentioned are mineral oils (liquid paraffin), vegetable oils (liquid fraction of karite butter, sunflower oil), animal oils (perhydrosqualene), synthetic oils (Purcellin oil), siliconized oils or waxes (cyclomethicone) and fluorinated oils (perfluoropolyethers), beeswax, carnauba wax or paraffin wax. It is possible to add to these oils fatty alcohols and fatty acids (stearic acid).

Emulsifiers which can be used in the invention and which can be mentioned are, for example, glycerol stearate, polysorbate 60 and the mixture of PEG-6/PEG-32/Glycol Stearate sold under the name of Tefose® 63 by Gattefosse.

Solvents which can be used in the invention and which can be mentioned are the lower alcohols, especially ethanol and isopropanol, and propylene glycol.

Hydrophilic gelling agents which can be used in the invention and which can be mentioned are the carboxyvinyl polymers (carbomer), the acrylic copolymers such as acrylate/alkylacrylate copolymers, polyacrylamides, polysaccharides such as hydroxypropylcellulose, natural rubbers and clays, and lipophilic gelling agents which can be mentioned are modified clays such as bentonites, metal salts of fatty acids such as aluminium stearates and hydrophobic silica, ethylcellulose and polyethylene.

The composition can contain other hydrophilic active agents such as proteins or protein hydrolysates, amino acids, polyols, urea, allantoin, sugars and sugar derivatives, water-soluble vitamins, plant extracts and hydroxyacids.

Lipophilic active agents which can be used are retinol (vitamin A) and its derivatives, tocopherol (vitamin E) and its derivatives, essentially fatty acids, ceramides, essential oils, salicylic acid and its derivatives.

According to the invention, the composition can comprise other active agents intended especially for the prevention and/or the treatment of cutaneous disorders. Among these active agents, it is possible to mention by way of example:

agents decreasing cutaneous differentiation and/or proliferation such as retinoic acid and its isomers, retinol and its esters, vitamin D and its derivatives, oestrogens such as oestradiol;

antibacterial agents such as clindamycin phosphate, erythromycin or antibiotics of the tetracycline class;

antiparasitic agents, in particular metronidazole, crotamiton or pyrethroids;

antifungal agents, in particular compounds belonging to the imidazoles class such as econazole, ketoconazole or miconazole or their salts, polyene compounds, such as amphotericin B, compounds of the allylamine family, such as terbinafine, or alternatively octopirox;

antiviral agents such as acyclovir;

steroidal anti-inflammatory agents, such as hydrocortisone, betamethasone valerate or clobetasol propionate, or non-steroidal anti-inflammatory agents such as ibuprofen and its salts, diclofenac and its salts, acetylsalicylic acid, acetaminophen or glycyrrhetic acid;

anaesthetic agents such as lidocaine hydrochloride and its derivatives;

antipruritic agents such as thenaldine, trimeprazine or cyproheptadine;

keratolytic agents such as α- and β-hydroxycarboxylic or β-ketocarboxylic acids, their salts, amides or esters and more particularly hydroxyacids such as glycolic acid, lactic acid, salicylic acid, citric acid and, generally speaking, fruit acids, and n-octanoyl-5-salicylic acid;

anti-free radical agents, such as α-tocopherol or its esters, superoxide dismutases, certain metal chelating agents or ascorbic acid and its esters;

antiseborrheic agents such as progesterone;

antidandruff agents such as octopirox or zinc pyrithione;

antiacne agents such as retinoic acid or benzoyl peroxide;

agents assisting the pigmentation of the skin and/or of the hair such as, for example, the substrates of at least one enzyme having a tyrosinase activity such as, for example tyrosine or its derivatives or 3,4-dihydroxyphenyl-α-alanine (DOPA), the derivatives of pyrimidine 3-oxide, substituted in the 6 position, such as, for example, those described in the patent application of the applicant filed in France under the number 96-11316 corresponding to the general

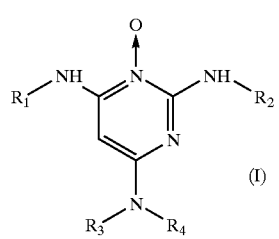

formula (I)

in which

R$_1$ and R$_2$, which are identical or different, are a hydrogen atom or a C$_1$–C$_{12}$ alkyl radical;

$R_3$ and $R_4$, which are identical or different, are a $C_1$–$C_{12}$ alkyl radical, or taken together can form a heterocycle with the nitrogen atom to which they are bonded;

it being understood that when R3 and R4 taken together form a piperidino cyclic system then at least one of the radicals R1 or R2 must be different from a hydrogen atom amongst which it is possible to mention particularly:

2-amino-4-propylamino-6-dimethylaminopyrimidine 3-oxide, 2-amino-4-methylamino-6-piperidinopyrimidine 3-oxide, 2,4-bis-propylamino-6-dimethylaminopyrimidine 3-oxide, 2,4-bis-propylamino-6-piperidinopyrimidine 3-oxide, 2,4-bis-methylamino-6-dimethylaminopyrimidine 3-oxide, 2,4-bis-ethylamino-6-dimethylaminopyrimidine 3-oxide;

extracts of bacterial origin such as, for example, extracts of non-photosynthetic filamentous bacteria such as, for example, extracts of *Vitreoscilla filiformis*.

Thus, the composition according to the invention can likewise comprise at least one agent selected from antibacterial, antiparasitic, antifungal, antiviral, anti-inflammatory, antipruritic, anaesthetic, keratolytic, anti-free radical, anti-seborrheic, antidandruff and antiacne agents, agents modulating cell differentiation and/or proliferation and/or agents assisting pigmentation of the skin and/or the hair.

It is likewise possible to envisage that the composition is in liposomal form, such as especially described in the Patent Application WO 94/22468 filed on Oct. 13, 1994 by the company Anti Cancer Inc. Thus, the compound encapsulated in the liposomes can be delivered selectively at the level of the hair follicle.

The invention likewise relates to a cosmetic treatment procedure for increasing the pigmentation of the skin and/or the hair such that a cosmetic composition comprising at least one extract of at least one plant of the genus Chrysanthemum is applied to the skin and/or the hair in a cosmetically acceptable medium.

Cosmetically acceptable medium is understood as meaning a medium compatible with the skin, the mucous membranes, the nails and the hair.

It is now intended to give, by way of illustration, examples which are not intended to limit, in any manner, the scope of the invention.

EXAMPLE 1

Preparation of an Extract of *Chrysanthemum morifolium* Variety Sinense

Leaves of plants of *Chrysanthemum morifolium* variety sinense cultivated in a greenhouse are taken and dried for 48 hours in a ventilated oven at a temperature of 45° C.

The dried leaves are then reduced to powder by grinding in a knife grinder of the Culatti type.

The powder obtained is sieved through a grille whose holes have a diameter of 1 mm. It is this sieved powder which is used for the preparation of the extract.

Protocol 1

The powder is mixed with an aqueous extraction solvent formed by cell culture medium DMEM/F 12.3:1 sold by the company Life Technologies, at a concentration rate of 5 grams of dry powder per 100 ml of solvent. The mixture is stirred for 4 hours at ambient temperature. The mixture is then centrifuged at 1000 revolutions/minute for 8 minutes and the supernatant is taken and subjected to two identical cycles of centrifugation/sampling. The last supernatant taken is filtered through a 0.22 μm filter of the Millipore type under aseptic conditions before being sterilized and kept at a temperature of 4° C. until use.

Protocol 2

The powder is mixed with sterile demineralized water having a pH of 6.5 at a concentration rate of 2.5 grams of dry powder per 100 ml of water. The mixture is stirred for 30 minutes at ambient temperature. The mixture is then filtered through GFD membranes sold by the company Whatmann and having a porosity of 0.7 μ. The filtrate obtained is then filtered through a 0.22 μm filter of Nalgene type under aseptic conditions before being sterilized and kept at a temperature of 4° C. until use.

Protocol 3

The previous protocol is carried out replacing the water by an aqueous extraction solvent formed by cell culture medium DMEM/F 12.3:1 sold by the company Life Technologies.

Protocol 4

The extract obtained in Protocol 2 is lyophilized at 30° C. before freezing at −20° C. The powder obtained is used directly.

EXAMPLE 2

Measurement of the Modulator Effect on the Melanogenesis of the Extract Obtained by Protocol 2 of Example 1

The modulator effect on melanogenesis of the extract obtained by Protocol 2 of Example 1 was tested on co-cultures of normal human keratinocytes/melanocytes according to the method described in the Patent FR 95 06491. The rate of synthesis of melanine is evaluated by the incorporation of thiouracil labelled with $C^{14}$. The synthesis of the proteins, determined by the incorporation of tritiated leucine, is taken as an indicator of cytotoxicity and of proliferation.

MATERIAL AND METHODS

Cell Cultures

The normal human keratinocytes (NHK) and the normal human melanocytes (NHM) are cultured from preputial skin. The two types of cells are proliferated and stored frozen. Eight days before the test, each of the cell types is again put into culture in KGM medium from Gibco for keratinocytes (NHK) and into M2 medium from Dr Olsson for melanocytes (NHM) (Olsson, M. J. et al., Lancet (1992) 340, 981). The media are changed every two days.

Forty-eight hours before confluence, the KGM medium of the NHK is replaced by a differentiation medium (DMEM/F 12 3:1, 10% calf serum, 10 ng/ml EGF, 0.4 μg/ml hydrocortisone, 5 μg/ml insulin).

Plant Extract

The plant extract of Example 1 (Protocol 2) is tested at the concentrations of $1.25 \ 10^{-4}$, $2.5 \ 10^{-4}$, $5 \ 10^{-4}$, $1.25 \ 10^{-3}$, $2.5 \ 10^{-3}$, $5 \ 10^{-3}\%$.

Modulation of Melanogenesis 250,000 normal human keratinocytes and 80,000 normal human melanocytes are mixed and sown in wells of 24-well plates (Costar type) and cultured for three days in the differentiation medium. During the three following days, the culture medium is replaced daily by the defined test medium (DMEM/F 12 3:1, 10 ng/ml epidermal growth factor (EGF), 10 ng/ml fibroblastic growth factor of type β (βFGF)) containing 1 μCi/ml of thiouracil labelled with $C^{14}$.

The following controls are carried out:

culture control: no product to be tested;

positive control of stimulation of melanogenesis: 1 mM tyrosine;

positive control of inhibition of melanogenesis: 0.5 mM kojic acid.

The total radioactivity incorporated in the proteins is estimated by the incorporation of tritiated leucine. The day before taking, 1 µCi/ml of tritiated leucine is added to the test medium.

After one night, the cells are rinsed in phosphate buffer. The proteins are precipitated with the aid of 5% trichloroacetic acid (TCA) and washed in order to eliminate the free radioactivity. The proteins are incubated overnight at 40° C. with the aid of a 100 µg/ml proteinase K solution in a tris HCl-triton-EDTA buffer. 50 µl of total extract are taken and transferred into a 24-well plate (Wallac) and 500 µl of scintillation fluid (Optiphase "Supermix") are added.

The remainder of the extract, or 950 µl, is filtered through a DEAE Filtermat filter. After rinsing, the "Meltilex" filter covered with the solid scintillant is transferred onto a plate. The radioactivity is counted with the aid of the Wallac counter. The results are expressed as a percentage of the control according to the formula:

$$\frac{(14CP/3HP)-(14CT/3HT)}{(14CT/3HT)} \times 100$$

in which:

$^{14}CP$ is the average of the disintegrations per minute (dpm) of $^{14}C$ thiouracil in 3 similar wells treated with a product (P);

$^{3}HP$ is the average of the corresponding $^{3}H$ leucine dpm;

$^{14}CT$ is the average of the $^{14}C$ thiouracil dpm in 3 similar control wells (T);

$^{3}HT$ is the average of the corresponding $^{3}H$ leucine dpm.

RESULTS:

| Products | $^{3}$HLeu. (%/control) | $^{14}$CThioU. (%/control) |
|---|---|---|
| 1 mM tyrosine | −2 | +118 |
| 5 10$^{-4}$% extract | −1 | +92 |
| 2.5 10$^{-3}$% extract | +5 | +502 |
| 5 10$^{-3}$% extract | −13 | +932 |
| 0.5 mM kojic acid | +4 | −47 |

CONCLUSIONS

This product is non-cytotoxic at the concentrations tested (non-significant variation of the incorporation of $^{3}$HLeu.) and induces the synthesis of melanine from 1.25 10$^{-3}$% (increase in the incorporation of $^{14}$CThioU.

EXAMPLE 3

Examples of Compositions Containing at Least One Extract of at Least One Plant of the Genus Chrysanthemum.

These compositions are obtained by the customary techniques currently used in cosmetics or in pharmacy.

| Dermal cream: | |
|---|---|
| Extract of Example 1, Protocol 1 | 5.000 g |
| Ceteareth 30 | 7.000 g |
| Glyceryl stearate | 2.000 g |
| Cetyl alcohol | 1.500 g |
| Polydimethylsiloxane | 1.500 g |
| Paraffin oil | 15.000 g |
| Glycerol codex pure | 20.000 g |
| Preservatives | q.s. |
| Demineralized water q.s. | 100.000 g |
| Dermal lotion for spraying: | |
| Extract of Example 1, Protocol 2 | 10.000 g |
| 3,4-Dihydroxyphenyl-α-alanine (DOPA) | 0.200 g |
| Ethanol | 30.000 g |
| Demineralized water q.s. | 100.000 g |
| Lotion for the hair: | |
| Extract of Example 1, Protocol 4 | 0.500 g |
| Tyrosine | 1.000 g |
| Propylene glycol | 30.000 g |
| Ethyl alcohol | 40.500 g |
| Water | qs. 100.000 g |

This lotion is applied to the scalp, one to two times per day, at a rate of 1 ml per application.

| Thickened lotion: | |
|---|---|
| Extract of Example 1, Protocol 3 | 15.000 g |
| Kawaine | 2.000 g |
| Hydroxypropylcellulose (Klucel G ® from Hercules) | 3.500 g |
| Ethyl alcohol | qsp 100.000 g |

This thickened lotion is applied to the scalp, one to two times per day, at a rate of 1 ml per application.

| Niosomal lotion: | |
|---|---|
| Extract of Example 1, Protocol 1 | 1.000 g |
| Chimexane NL ® | 0.475 g |
| Cholesterol | 0.475 g |
| Monosodium stearoylglutamate | 0.050 g |
| Preservatives | qs |
| Colorants | qs |
| Perfume | qs |
| Demineralized water | qs 100.000 g |

This lotion is applied to the scalp, one to two times per day, at a rate of 1 ml per application.

| Lotion: | |
|---|---|
| Extract of Example 1, Protocol 2 | 2.000 g |
| Tyrosine | 1.000 g |
| Propylene glycol monomethyl ether (Dowanol PM ® from Dow Chemical) | 20.000 g Hydro |
| Ethyl alcohol | 40.000 g |
| Minoxidil | 2.000 g |
| Water | qs 100.000 g |

This thickened lotion is applied to the scalp, one to two times per day, at a rate of 1 ml per application.

What is claimed is:

1. A method for stimulating melanogenesis, comprising topically applying to the skin and/or hair of an individual in need of stimulation of melanocytes, a cosmetic or pharmaceutical composition comprising an effective melanogenesis-stimulating amount of an aqueous, alcoholic, or aqueous/alcoholic extract of Chrysanthemum leaves in a cosmetically or pharmaceutically acceptable medium, said extract of Chrysanthemum leaves being the sole melanogenesis-stimulating agent in said composition.

2. The method according to claim 1, wherein said leaves are from at least one plant species selected from the group consisting of *Chrysanthemum hortorum, Chrysanthemum morifolium, Chrysanthemum coronarium, Chrysanthemum myconis, Chrysanthemum sagitum, Chrysanthemum indicum*, and *Chrysanthemum segetum*.

3. The method according to claim 2, wherein said leaves are from the species *Chrysanthemum morifolium*.

4. The method according to claim 3, wherein said leaves are from the variety sinense.

5. The method according to claim 1, wherein said extract is obtained from leaves which are cultivated in vivo.

6. The method according to claim 2, wherein said extract is obtained from leaves which are cultivated in vivo.

7. The method according to claim 3, wherein said extract is obtained from leaves which are cultivated in vivo.

8. The method according to claim 4, wherein said extract is obtained from leaves which are cultivated in vivo.

9. The method according to claim 1, wherein said extract is in a quantity representing from 0.01% to 15% of the total weight of the composition.

10. The method according to claim 2, wherein said extract is in a quantity representing from 0.01% to 15% of the total weight of the composition.

11. The method according to claim 3, wherein said extract is in a quantity representing from 0.01% to 15% of the total weight of the composition.

12. The method according to claim 4, wherein said extract is in a quantity representing from 0.01% to 15 % of the total weight of the composition.

13. The method according to claim 9, wherein said extract is in a quantity representing from 1% to 5% of the total weight of the composition.

14. The method according to claim 10, wherein said extract is in a quantity representing from 1% to 5% of the total weight of the composition.

15. The method according to claim 11, wherein said extract is in a quantity representing from 1% to 5% of the total weight of the composition.

16. The method according to claim 12, wherein said extract is in a quantity representing from 1% to 5% of the total weight of the composition.

* * * * *